(12) United States Patent
Dolitzky et al.

(10) Patent No.: US 6,924,393 B2
(45) Date of Patent: Aug. 2, 2005

(54) CRYSTALLINE VENLAFAXINE BASE AND NOVEL POLYMORPHS OF VENLAFAXINE HYDROCHLORIDE, PROCESSES FOR PREPARING THEREOF

(75) Inventors: Ben-Zion Dolitzky, Petach Tiqva (IL); Judith Aronhime, Rehovot (IL); Shlomit Wizel, Petah Tikva (IL); Gannady A. Nisnevich, Haifa (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 10/961,337

(22) Filed: Oct. 7, 2004

(65) Prior Publication Data

US 2005/0049304 A1 Mar. 3, 2005

Related U.S. Application Data

(60) Division of application No. 10/000,428, filed on Nov. 30, 2001, now abandoned, which is a continuation-in-part of application No. 10/045,510, filed on Oct. 19, 2001.
(60) Provisional application No. 60/241,577, filed on Oct. 19, 2000, provisional application No. 60/258,861, filed on Dec. 29, 2000, provisional application No. 60/278,721, filed on Mar. 26, 2001, and provisional application No. 60/292,469, filed on May 21, 2001.

(51) Int. Cl.$^7$ .......................................... C07C 211/00
(52) U.S. Cl. ........................................................ 564/336
(58) Field of Search ......................................... 564/336

(56) References Cited

U.S. PATENT DOCUMENTS

4,611,078 A  9/1986  Husbands et al.

FOREIGN PATENT DOCUMENTS

| WO | WO 00/32555 | 6/2000 |
| WO | WO 02/36542 A1 | 5/2002 |
| WO | WO 02/46140 A1 | 6/2002 |

OTHER PUBLICATIONS

J.P. Yardley, et al., 2–Phenyl–2–(1–hydroxycycloalkyl)–ethylamine Derivatives: Synthesis and Antidepressant Activity, Journal of Medicinal Chemistry, 1990, 33, pp. 2899–2905.

Daniel Vega et al., 1–[2–(1–Hydroxycyclohexyl)–2–(4–methoxyphenyl)ethyl]dimethyl–ammonium chloride (venlafaxine hydrochloride), Acta Crystallographica Section C Crystal Structure Communications, 2000, C56, pp. 1009–1010.

*Primary Examiner*—Samuel Barts
(74) *Attorney, Agent, or Firm*—Kenyon & Kenyon

(57) ABSTRACT

The present invention relates to novel essentially pure venlafaxine and the process of preparation thereof. The present invention also relates to novel solvate forms of venlafaxine hydrochloride and the process of preparation thereof. Furthermore, the present invention provides a novel process for preparing venlafaxine hydrochloride from venlafaxine; the process comprises the steps of: i) preparing a mixture of venlafaxine with acetone; and ii) exposing the mixture in gaseous hydrochloric acid.

6 Claims, 10 Drawing Sheets

CRYSTALLINE VENLAFAXINE BASE AND NOVEL POLYMORPHS OF VENLAFAXINE HYDROCHLORIDE, PROCESSES FOR PREPARING THEREOF

CROSS-REFERENCE OF RELATED APPLICATIONS

This application is a divisional application of U.S. application Ser. No. 10/000,428, filed Nov. 30, 2001 now abandoned as a continuation-in-part of U.S. patent application Ser. No. 10/045,510, filed Oct. 19, 2001 entitled "Crystalline venlafaxine base and novel polymorphs of venlafaxine hydrochloride, processes for preparing thereof" by Ben-Zion Dolitzky, Judith Aronhime, Shlomit Weizel, and Gennady Nisnevish which claims priority of the Provisional Application Ser. Nos. 60/241,577 filed Oct. 19, 2000, 60/258,861 filed Dec. 29, 2000, 60/278,721 filed Mar. 26, 2001 and 60/292,469 filed May 21, 2001. The content of these applications is herein incorporated by reference in their entireties.

BACKGROUND OF THE INVENTION

Venlafaxine, (±)-1-[2-(Dimethylamino)-1-(4-ethyoxyphenyl)ethyl]cyclo-hexanol, having the following formula I, is the first of a class of anti-depressants. Venlafaxine acts by inhibiting re-uptake of norepinephrine and serotonin, and is an alternative to the tricyclic anti-depressants and selective re-uptake inhibitors.

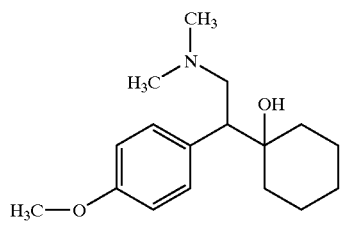

I

U.S. Pat. No. 4,535,186 (the '186 patent) describes the process for the preparation of venlafaxine hydrochloride via the intermediate venlafaxine base. The entirety of the '186 patent is incorporated herein by reference. However, the '186 patent does not describe whether the venlafaxine so obtained is solid.

The existence of certain polymorphs of venlafaxine hydrochloride is mentioned in the European patent application EP 0 797 991 A1.

In the Summary Basis of Approval of New Drug Application No. 20-151 (venlafaxine hydrochloride tablets) and No. 20-699 (venlafaxine extended release capsules), three polymorphic forms of venlafaxine hydrochloride are mentioned.

We have now found a novel process for isolating venlafaxine as a solid. The isolated venlafaxine is in the form of white crystals, with a purity of 99.3% or greater as confirmed by high pressure liquid chromatography (HPLC).

We have found that crystalline venlafaxine can be prepared from venlafaxine hydrochloride by methylation of N,N-didesmethyl venlafaxine by means of a novel process.

We have found two novel polymorphs of venlafaxine hydrochloride (denominated Form I and Form II) and two novel solvate forms (denominated Form III and IV).

We have found a process for preparing venlafaxine hydrochloride from venlafaxine base and hydrochloric acid (HCl) gas in acetone or isopropanol. We have found the application of such process for preparing venlafaxine hydrochloride Form I and Form II.

SUMMARY OF THE INVENTION

According to one aspect, the present invention relates to an essentially pure venlafaxine.

According to another aspect, the present invention relates to an essentially pure venlafaxine hydrochloride.

According to another aspect, the present invention provides a process of preparing venlafaxine base from venlafaxine hydrochloride.

According to another aspect, the present invention provides a process of preparing venlafaxine base by alkylation of N,N-didesmethyl venlafaxine.

According to another aspect, the present invention provides crystalline venlafaxine base, wherein the venlafaxine base is white crystal with about 97% purity.

According to another aspect, the present invention provides crystalline venlafaxine base, wherein the venlafaxine base is white crystal with about 98% purity.

According to another aspect, the present invention provides crystalline venlafaxine base, wherein the venlafaxine base is white crystal with about 99% purity.

According to another aspect, the present invention provides crystalline venlafaxine base, wherein the venlafaxine base is white crystal with about 99.3% purity.

According to another aspect, the present invention provides crystalline venlafaxine base, wherein the venlafaxine base is white crystal with about 99.5% purity.

According to one aspect, the present invention relates to a process for the preparation of an essentially pure venlafaxine hydrochloride via the solid venlafaxine.

According to another aspect, the present invention relates to two novel polymorphs of venlafaxine hydrochloride denominated as Form I and Form II as well as solvate forms of venlafaxine hydrochloride denominated as Form III and Form IV.

According to another aspect, the present invention provides a process for preparation of the anhydrous Form I by dissolving the compound in water and precipitating it by adding DMF (dimethyl formamide) or MEK (methylethylketone).

According to another aspect, the present invention provides a process for preparation of the solvate Form III by dissolving the compound in a protic solvent such as water, ethanol or methanol and precipitating it by adding an aprotic solvent like acetone, ethylacetate, isopropylether or tert-butylmethylether (MTBE).

According to another aspect, the present invention provides a process for preparation of the solvate Form III by dissolving the compound in chloroform and precipitating it by adding hexane or toluene.

According to another aspect, the present invention provides processes for preparation of the solvate Form III by crystallizing the compound in absolute ethanol or isopropyl alcohol.

According to another aspect, the present invention provides processes for preparation of the solvate Form III by triturating the compound in aprotic solvents such as ethyl acetate, isopropyl ether or hexane.

According to another aspect, the present invention provides processes for preparation of the solvate Form IV by crystallizing the compound in DMF (dimethyl formamide)

and DMSO (dimethyl sulfoxide), or by dissolving the compound in water and precipitating it by adding DMSO.

According to yet another aspect, the present invention provides a process for preparing venlafaxine hydrochloride from venlafaxine base.

According to another aspect, the present invention provides a process of preparing venlafaxine hydrochloride comprises the step of forming a mixture of venlafaxine, preferably venlafaxine base, in acetone and exposing the mixture in gaseous hydrochloric acid (HCl).

According to another aspect, the present invention provides a process of preparing venlafaxine hydrochloride comprises the step of forming a mixture of venlafaxine, preferably venlafaxine base, in isopropanol and introducing hydrochloric acid (HCl), preferably gaseous hydrochloric acid, until a pH is in the range of about 5 to about 8. Preferable pH is about 6 to about 7.5. Most preferable pH is about 7.

According to another aspect, the present invention provides a process of preparing venlafaxine hydrochloride comprises exposing a homogeneous solution of venlafaxine/acetone in gaseous hydrochloric acid (HCl).

According to another aspect, the present invention provides a process of preparing venlafaxine hydrochloride comprises exposing a homogeneous solution of venlafaxine/isopropanol in gaseous hydrochloric acid (HCl).

According to another aspect, the present invention provides preparing a homogenous solution of venlafaxine in a solution where venlafaxine is substantially insoluble or limited solubility, preferably acetone or isopropanol.

According to another aspect, the present invention provides processes for preparing venlafaxine Form I and Form II.

According to another aspect, the present invention provides a process for preparing venlafaxine hydrochloride comprising the steps of: 1) preparing a mixture (or a homogeneous solution) of venlafaxine, preferably venlafaxine base, with acetone; and 2) exposing the mixture in gaseous hydrochloric acid (HCl).

According to another aspect, the present invention provides a process for preparing venlafaxine hydrochloride comprising the steps of: 1) preparing a mixture of venlafaxine in isopropanol; and 2) exposing the mixture in gaseous hydrochloric acid at a range of pH. The pH ranges from about pH 5 to about pH 8. Preferably the pH ranges from about pH 6 to about pH 7.5. Most preferably the pH is at about pH 7.

According to another aspect, the present invention provides venlafaxine hydrochloride, where the venlafaxine hydrochloride is white crystal with about 99.92% purity.

According to another aspect, the present invention provides a process for preparing venlafaxine hydrochloride Form I comprises triturating venlafaxine hydrochloride with acetone followed by drying upon stirring under reduced pressure and crystallizing venlafaxine hydrochloride.

According to another aspect, the present invention provides venlafaxine hydrochloride Form I as prepared by a process comprises triturating venlafaxine hydrochloride with acetone followed by drying upon stirring under reduced pressure and crystallizing venlafaxine hydrochloride.

According to another aspect, the present invention provides a process for preparing venlafaxine hydrochloride Form I comprises triturating venlafaxine hydrochloride with isopropanol followed by drying upon stirring under reduced pressure and crystallizing venlafaxine hydrochloride.

According to another aspect, the present invention provides venlafaxine hydrochloride Form I as prepared by a process comprises triturating venlafaxine hydrochloride with isopropanol followed by drying upon stirring under reduced pressure and crystallizing venlafaxine hydrochloride.

According to another aspect, the present invention provides venlafaxine hydrochloride Form I, where the venlafaxine hydrochloride Form I is white crystal with about 99.95% purity.

According to another aspect, the present invention provides a process for preparing venlafaxine hydrochloride Form II comprises triturating venlafaxine hydrochloride with acetone or isopropanol followed by drying in a tray under reduced pressure and crystallizing venlafaxine hydrochloride.

According to another aspect, the present invention provides venlafaxine hydrochloride Form II as prepared by a process of triturating venlafaxine hydrochloride with acetone or isopropanol followed by drying in a tray under reduced pressure and crystallizing venlafaxine hydrochloride.

According to another aspect, the present invention provides venlafaxine hydrochloride Form II where the venlafaxine hydrochloride Form II is white crystal with about 99.95% purity.

DETAILED DESCRIPTION OF THE INVENTION

Figure 1:
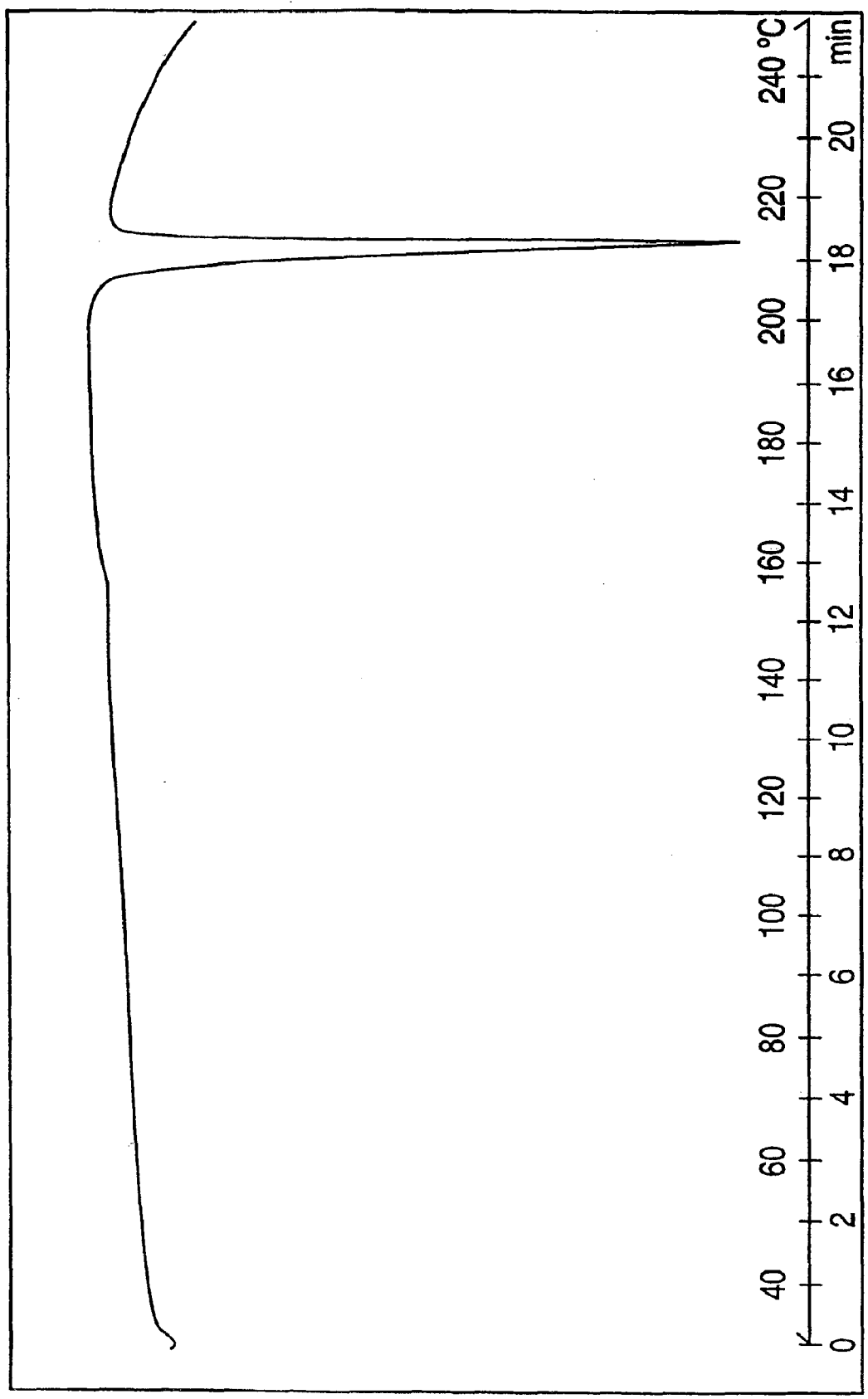
FIG. 1 represents the Differential Scanning Calorimetry (DSC) curve of Venlafaxine Hydrochloride Form I.
Figure 2:
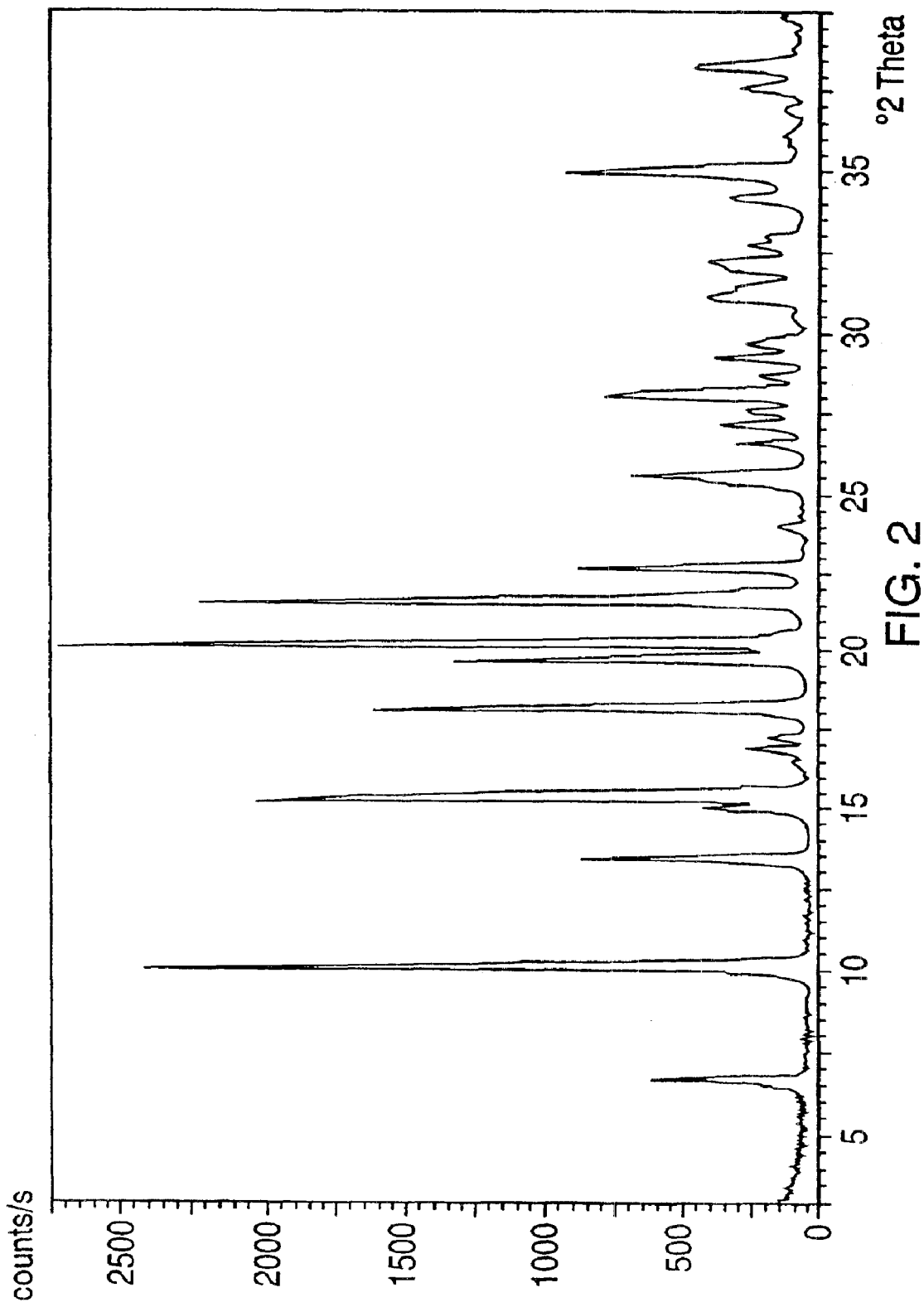
FIG. 2 represents the powder x-ray diffractogram (PXRD) of Venlafaxine Hydrochloride Form I.
Figure 3:
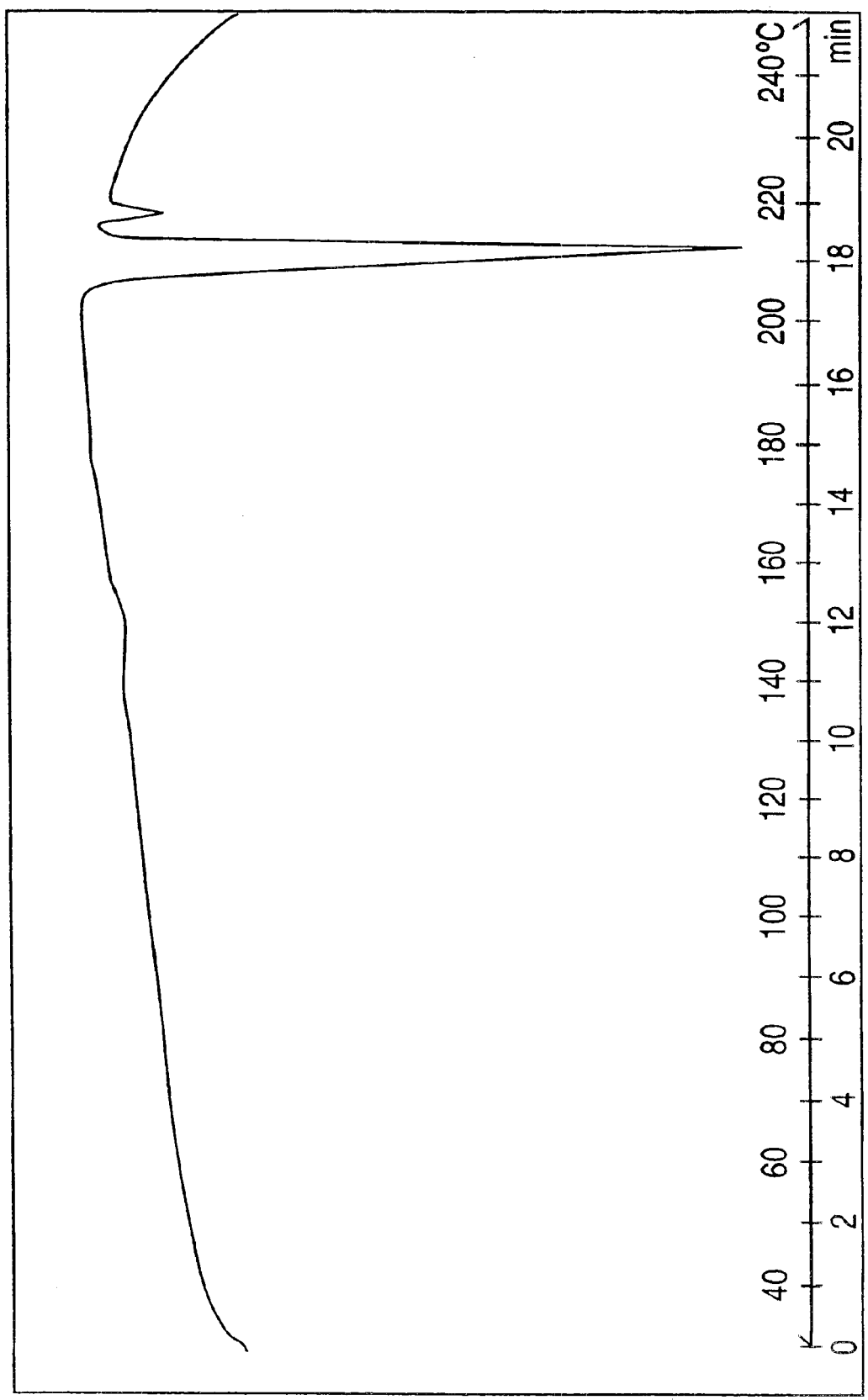
FIG. 3 represents the DSC curve of Venlafaxine Hydrochloride Form II.
Figure 4:
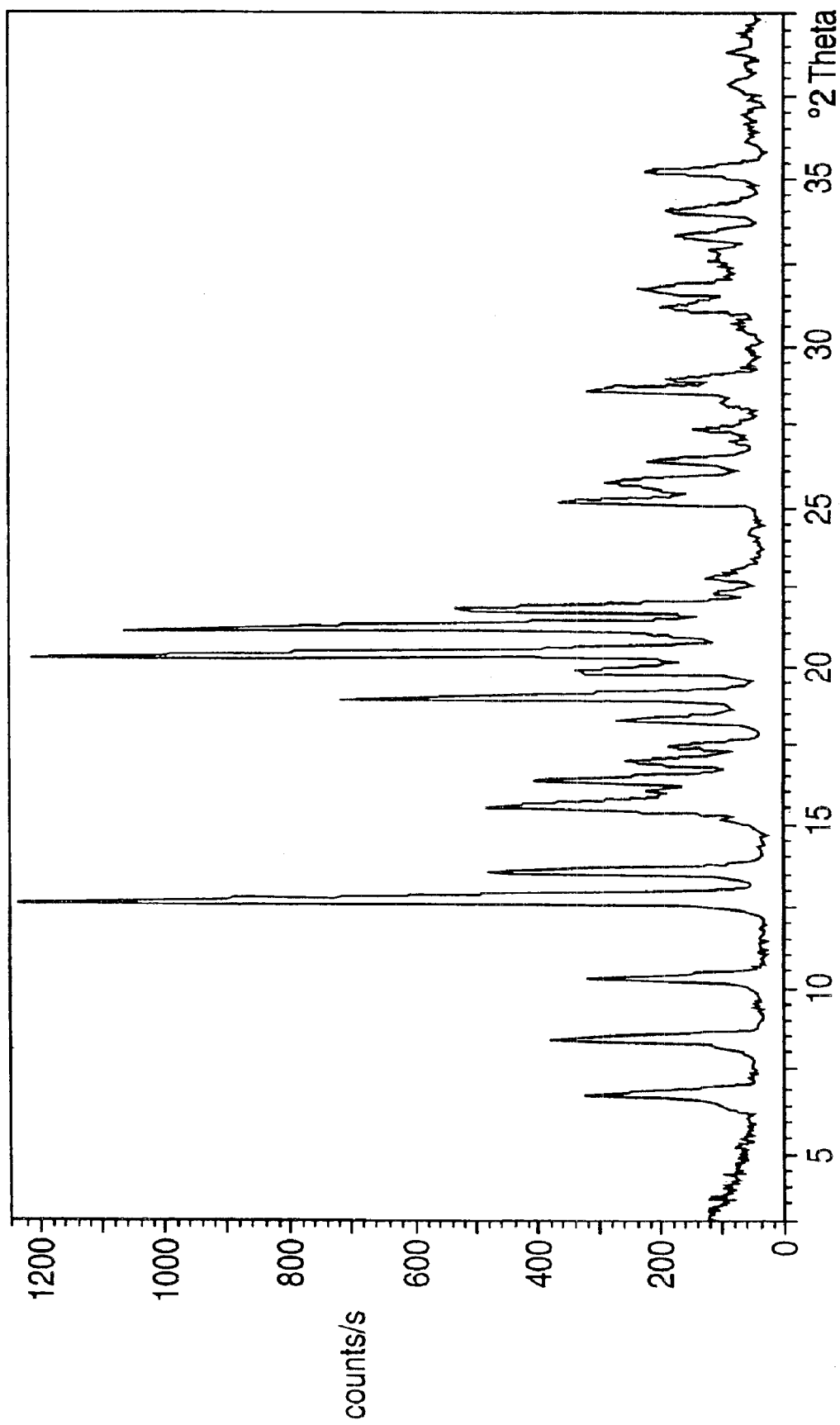
FIG. 4 represents the PXRD of Venlafaxine Hydrochloride Form II.
Figure 5:
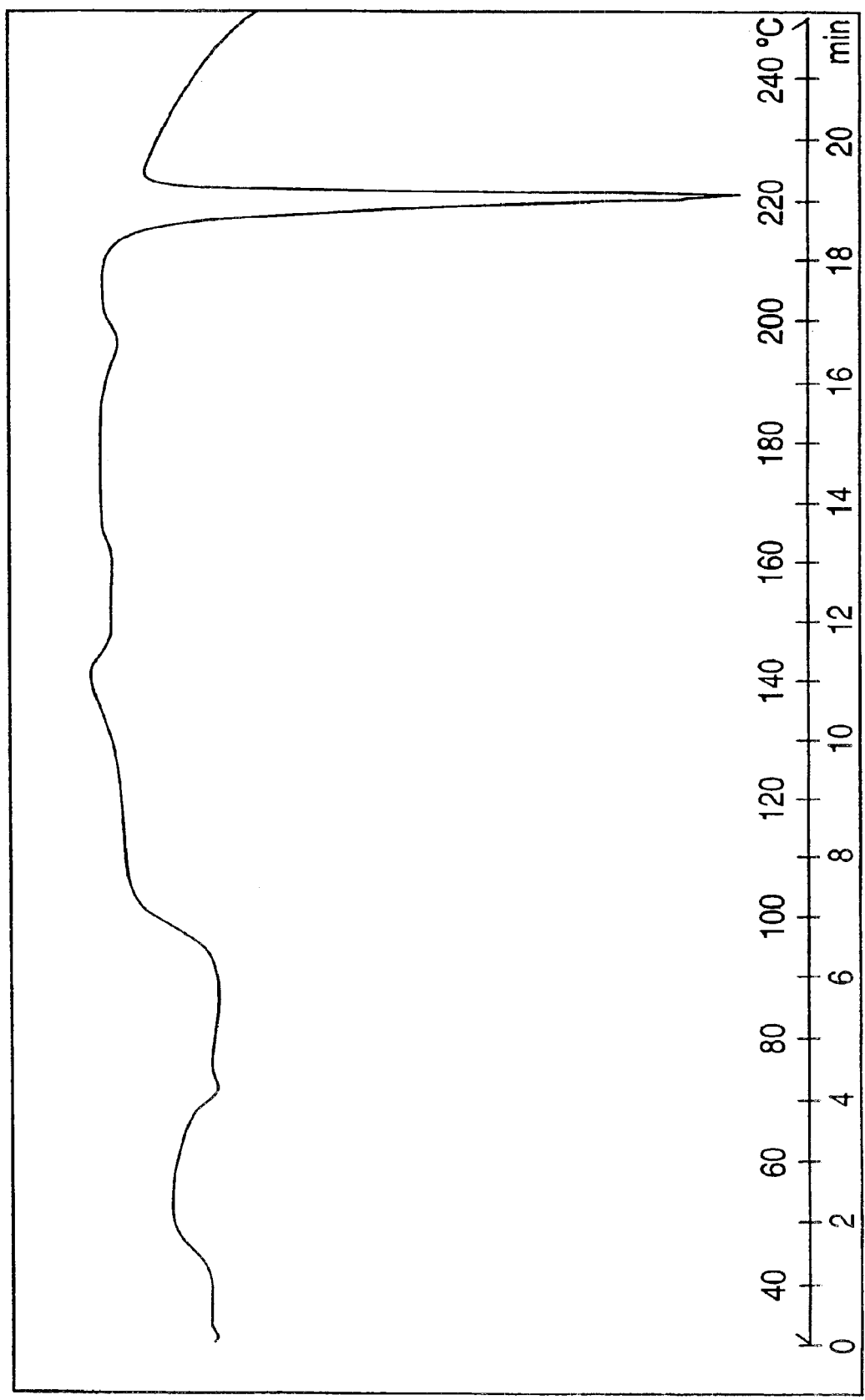
FIG. 5 represents the DSC curve of Venlafaxine Hydrochloride Form III.
Figure 6:
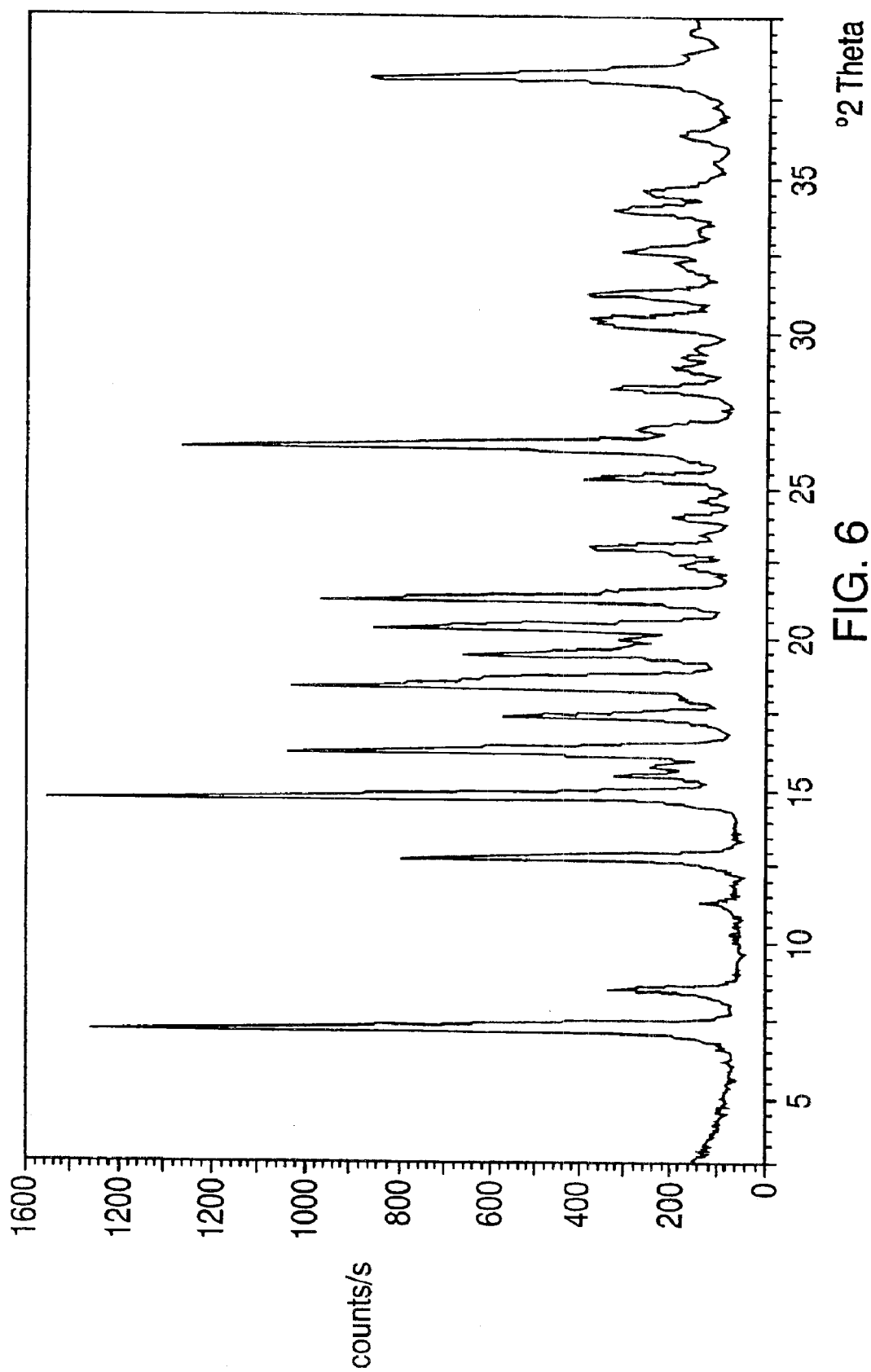
FIG. 6 represents the PXRD of Venlafaxine Hydrochloride Form III.
Figure 7:
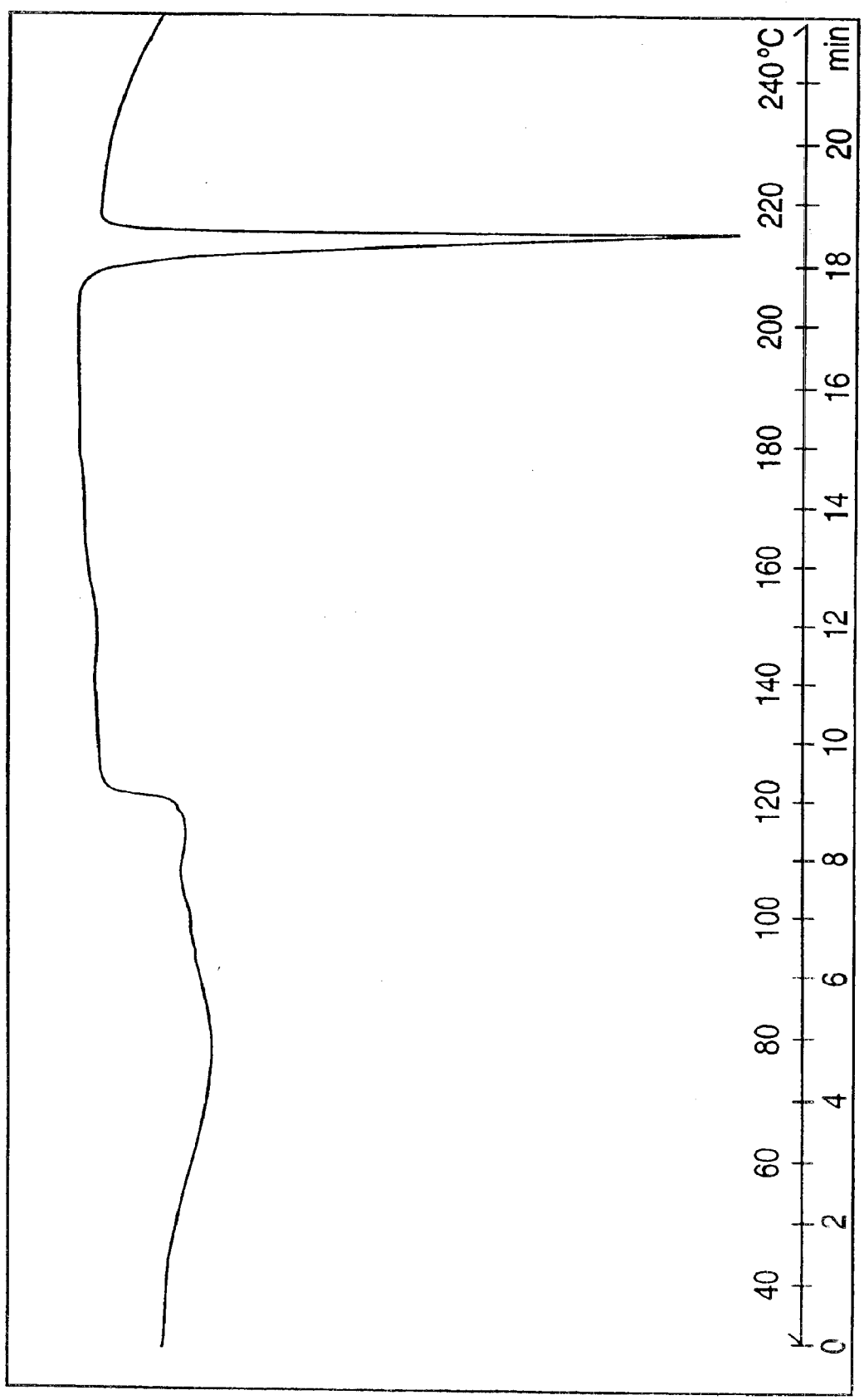
FIG. 7 represents the DSC curve of Venlafaxine Hydrochloride Form IV.
Figure 8:
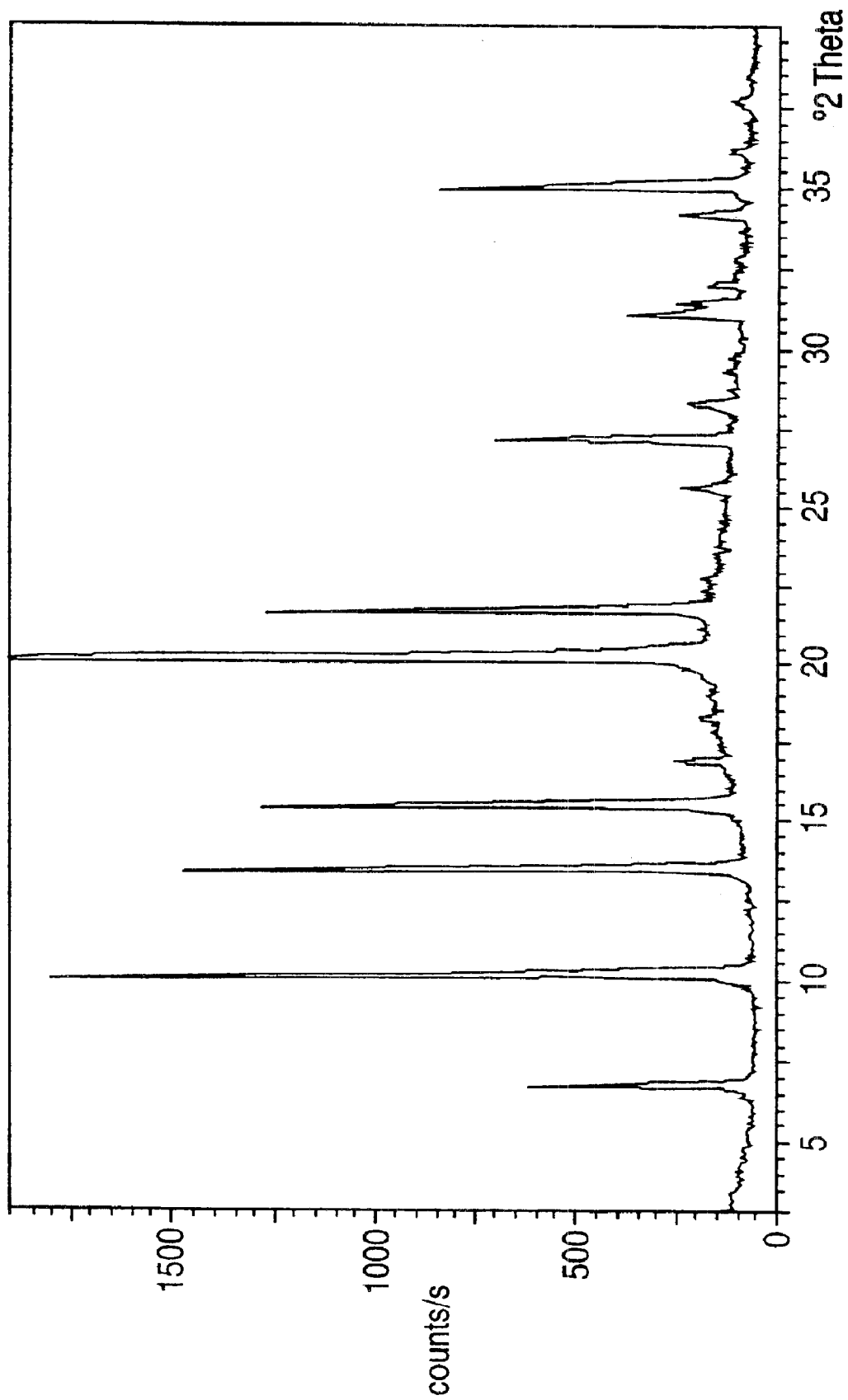
FIG. 8 represents the PXRD of Venlafaxine Hydrochloride Form IV.
Figure 9:
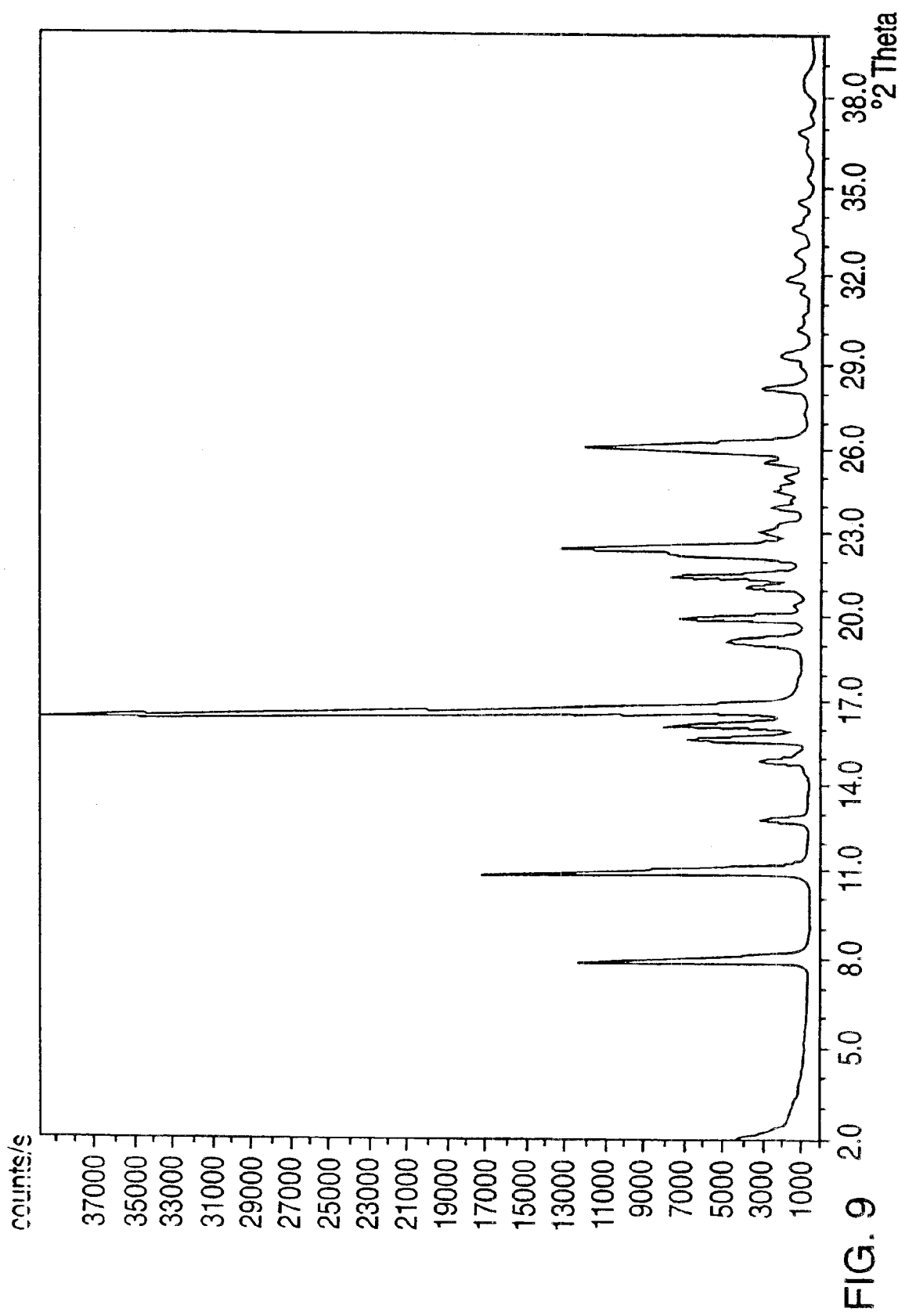
FIG. 9 represents the PXRD of crystalline Venlafaxine Base.

As used herein, the following abbreviated terms are: "DMF" refers to dimethyl formamide; "MEK" refers to methylethylketone; "MTBE" refers to tert-butylmethylether; "DMSO" refers to dimethyl sulfoxide; "DSC" refers to Differential Scanning Calorimetry; "PXRD" refers to powder x-ray diffractogram; "IPA" refers to isopropyl alcohol; and "HCl" refers to hydrochloric acid.

I) Venlafaxine Free Base

The present invention relates to essentially pure venlafaxine which, surprisingly, can be obtained in the form of free base. The venlafaxine base exists in a solid crystalline form.

An essentially pure venlafaxine is prepared by adding sodium hydroxide to an aqueous solution of venlafaxine

5 hydrochloride. Another preferable alkali solution is potassium hydroxide. The resulting mixture was extracted by an organic solvent. The extraction can be performed using ethyl acetate, heptane, hexane and a mixture thereof. The extraction solvent is preferably ethyl acetate. The combined organic layers are dried, preferably over anhydrous sodium sulfate, and evaporated. The residue is then crystallized from hexane or heptane.

The crystals so obtained are filtered off, washed with cold hexane or heptane and dried to give solid venlafaxine, with purity of 99.3% or greater. The purity of solid venlafaxine is generally greater than about 97%, preferably greater than about 98% and most preferably greater than about 99%.

The solid venlafaxine is further reacted with hydrochloric acid and crystallized to yield an essentially pure venlafaxine hydrochloride.

The invention is further described in the following examples which are in no way intended to limit the scope of the invention.

EXAMPLE 1

Sodium hydroxide, 32% aq. solution (10.0 grams, 80.0 mmol) was added to a stirred solution of venlafaxine hydrochloride (20.0 grams, 63.7 mmol) in water (100 mL) in an ice-water bath. The mixture was stirred in an ice/water bath for about 30 min and extracted with ethyl acetate (3×30 mL). The combined organic layers were dried over anhydrous sodium sulfate, filtered and evaporated under reduced pressure at about 50–60° C. (water bath). The residue was dissolved in boiling hexane (50 mL) and cooled in a freezer (−18° C.).

The crystals so obtained were filtered off, washed with cold hexane (20 mL) and dried under reduced pressure to give 15.5 grams (87.7%) of venlafaxine as white crystals with about 99.3% purity by HPLC, mp 78.3–79.5° C.

EXAMPLE 2

Preparation of a Crystalline Venlafaxine Free Base from N,N-didesmethyl Venlafaxine Hydrochloride

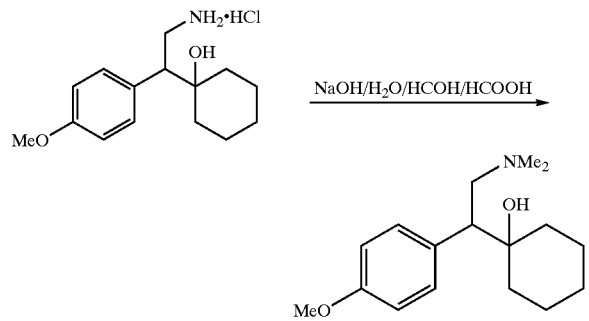

Sodium hydroxide, 32% aq. solution (2.75 gram, 0.022 mol) was added to a stirred solution of N,N-didesmethyl venlafaxine hydrochloride (5.72 gram, 0.02 mol) in water in water (13 mL) at room temperature. Formic acid, 88.5% aq. solution (4.16 gram, 0.08 mol) and formaldehyde solution 35.8% aq. solution (3.7 gram, 0.044 mol) were added to this emulsion. The obtained mixture was stirred under reflux conditions during 8 hours cooled to room temperature, adjusted to pH~11 with 32% aq. solution of sodium hydroxide and extracted with heptane (100 mL).

An organic extract was washed with water (20 mL), dried over sodium sulfate and evaporated two volumes and filtered to give crystalline venlafaxine base.

EXAMPLE 3

Preparation of Venlafaxine Base

N,N-didesmethyl venlafaxine (20 mmole) was added to water (480 mL), formic acid (88.5%, 5.2 grams,~100 mmole), formaldehyde (35.8%, 5 grams, 62 mmole) at room temperature. The obtained mixture was stirred under reflux conditions during 21 hours and cooled to room temperature. The pH was adjusted to about 11 with 32% aqueous solution of NaOH. Potassium hydroxide can be equivalently used to adjust to pH to about 11. The pH-adjusted mixture was extracted with toluene (50 mL×5).

The combined organic phages were washed with water (50 mL), dried over sodium sulfate and evaporated to dryness to give crystalline venlafaxine base (5.4 grams, 98%). The purity determined by HPLC was about 99.5%. The material can be crystallized from hexane, pentane, petroleium-ether and the like. The melting point of crystalline venlafaxine base ranges from 78.3–79.5° C.

II) Venlafaxine Hydrochloride

The present invention provides a process for the purification of venlafaxine hydrochloride comprising basifying the venlafaxine hydochloride.

The present invention provides a process for the purification of venlafaxine hydochloride further comprising crystallizing the venlafaxine.

The present invention provides a process for the purification of venlafaxine hydochloride further comprising reacting the venlafaxine so prepared with hydrochloric acid and crystallization to regenerate venlafaxine hydrochloride in a higher state of purity. The purity of venlafaxine hydrochloride is generally greater than about 97%, preferably greater than 98% and most preferably greater than about 99%.

Venlafaxine hydrochloride is obtained according to the process as described in U.S. Pat. No. 4,535,186, which is incorporated herewith in reference.

III) Novel Solvate And Polymorphic Forms Of Venlafaxine Hydrochloride:

Venlafaxine Hydrochloride Form I

According to one aspect, the present invention relates to a novel polymorphic form of venlafaxine hydrochloride, denominated Form I. This crystal form is characterized by unique strong X-ray peaks at about 10.2, 15.5, 20.3, 21.7±0.2 degrees two-theta, and medium peaks at 6.7, 13.5, 18.2, 19.8, 22.6, 25.6, 28.1, 35.1±0.2 degrees two-theta.

The DSC thermogram of Form I includes an endotherm at about 210–213 degrees due to melting.

Venlafaxine Hydrochloride Form II

According to another aspect, the present invention relates to a novel polymorphic form of venlafaxine hydrochloride, denominated Form II. This crystal form is characterized by unique strong X-ray peaks at about 12.8, 20.5, 21.3±0.2 degrees two-theta, and medium peaks at 6.8, 8.5, 10.3, 13.6, 15.6, 16.5, 19.8, 19.9, 21.9, 25.2, 28.7, 31.2, 31.7, 35.3±0.2 degrees two-theta.

The DSC thermogram of Form II includes an endotherm at about 210–213 degrees due to melting; a phase transformation is often observed with a resulting peak at about 219–222 degrees. This transformation may occur at different extents and probably is concomitant to a sublimation phenomenon.

Venlafaxine Hydrochloride Form III

According to another aspect, the present invention relates to a novel solvate crystal form of venlafaxine hydrochloride, denominated Form III. This crystal form is characterized by unique strong X-ray peaks at about 7.4, 14.9, 26.5±0.2 degrees two-theta, and medium peaks at about 12.9, 16.4, 17.5, 18.6, 18.9, 20.5, 21.4, 38.2±0.2 degrees two-theta.

The DSC thermogram of Form III includes a broad endotherm due to desolvatation, a small endotherm in the range of approximately 180–200 degrees and an endotherm at about 212 degrees, due to melting.

This solvated form may include water, or methanol, ethanol or hexane. The loss on drying values range between about 5.6%–6.0% for the compounds that contain methanol or ethanol, about 4.6% for the compound that contains isopropyl alcohol, and about 5.5% for the compound that contains hexane.

These values indicate a stoichiometric composition of about ½ molecule of methanol or ethanol and ¼ molecule of isopropyl alcohol per molecule of venlafaxine hydrochloride. These data point to the presence of hemisolvates of ethanol or methanol, and ¼ solvate of isopropyl alcohol.

Venlafaxine Hydrochloride Form IV

According to another aspect the present invention relates to a novel solvate crystal form of venlafaxine hydrochloride, denominated Form IV. This crystal form is characterized by unique strong X-ray peaks at about 10.3, 20.3±0.2 degrees two-theta, and medium peaks at about 6.8, 13.5, 15.6, 21.8, 27.2, 35.2±0.2 degrees two-theta.

The DSC thermogram of Form IV includes a broad endotherm due to desolvatation, and an endotherm at about 212 degrees due to melting.

This solvated crystal form may include DMSO or DMF. The loss on drying value, as determined in the TGA, is about 41% in the compound crystallized in DMSO, and about 33% in the compound crystallized in DMF. These values—about 41% and 33%—correspond to the stoichiometric values of 3 molecules of DMSO and 2 molecules of DMF per molecule of Venlafaxine hydrochloride. From this we deduce that solvated Form IV may be a trisolvate of DMSO and disolvate of DMF.

IV) Preparation of Polymorphs of Crystalline Venlafaxine Hydrochloride

The present invention discloses processes for preparation of the different polymorphic forms of venlafaxine hydrochloride.

It was observed that the polymorphic novel forms (denominated Form I and Form II) are obtained by a transformation of the solvate forms during the drying process.

It was observed that crystallization produces novel solvated forms (denominated Form III and Form IV).

It was observed that the drying process of the solvate Forms III and IV may lead to either Form I, Form II or a mixture of the two forms. By using a rotavapor, in which the drying conditions involve reduced pressure, continuous revolving of the powder, and moderate heat—about 60 degrees—mainly Form I is obtained, but in few cases Form I or a mixture of Form I and Form II are also obtained. By drying the solvate forms in a static oven—about 160 degrees ½ hour—Form III transformed to Form II, and Form IV transformed to Form I.

It was observed that Form III can form solvates with different solvents, such as ethanol, methanol, or isopropanol.

It was observed that Form IV can form solvates with DMF and DMSO.

A process in which a novel solvate Form III can be produced was observed. In this process, venlafaxine hydrochloride is dissolved in protic solvents (i.e., solvents that have a hydroxide [—OH] group) like water, ethanol or methanol, and an aprotic solvent (i.e., a solvent that lacks a hydroxide [—OH] group) such as acetone, ethyl acetate, isopropyl ether or tert-butylmetylether (MTBE) is added to produce solvate Form III. By further drying the sample in a rotavapor under reduced pressure (~10 mbar) over about 45 minutes at about 60 degrees, novel polymorphic Form I is obtained.

It was observed that a process in which venlafaxine hydrochloride is dissolved in chloroform, and to that solution DMF or DMSO is added, produced the novel solvate Form III. By further drying the sample in a rotavapor under reduced pressure (~10 mbar) over about 45 minutes at about 60 degrees, novel polymorphic Form I is obtained.

Direct crystallization in ethanol, isopropyl alcohol, chloroform, also produces Form II, which by further drying the sample in a rotavapor under reduced pressure (~10 mbar) over about 45 minutes at about 60 degrees, novel polymorphic Form I or a mixture of Forms I and II is obtained.

Direct crystallization from DMF and DMSO produces novel solvate Form IV which by further drying the sample in a rotavapor under reduced pressure (~10 mbar) over about 45 minutes at about 60 degrees, novel polymorphic Form II or a mixture of Forms I and II is obtained.

It was observed that a process in which venlafaxine hydrochloride is dissolved in water, and to that solution MEK or DMF are added, produced the novel polymorphic Form I.

It was observed that a process in which venlafaxine hydrochloride is dissolved in methanol, and to that solution ethyl acetate in the ratio about 3:30 solvent:antisolvent is added, produced the novel polymorphic Form II.

It was observed that a process in which venlafaxine hydrochloride is dissolved in isopropanol, and to that solution exposed in gaseous hydrochloric acid at a range of pH. The pH ranges from about pH 5 to about pH 8. Preferably the pH ranges from about pH 6 to about pH 7.5. Most preferably the pH is at about pH 7.

Methods

PXRD

X-Ray Difractometer, Phillips Generator TW1830
Goniometer PW3020
MPD Control PW3710
X-Ray tube with Cu target anode
Monochromator proportional counter
Divergence slits 1°, Receiving slit 0.2 mm, Scatter slit 1°
Power:40 KV, 30 mA
Scanning speed: 2 deg/min step: 0.05 deg

TGA

DTG-50, Shimadzu
Sample weight: 7–15 mg
Temperature range: up to 185° C.
Heating rate: 10° C./min

DSC

DSC821®, Mettler Toledo
Sample weight: 3–5 mg
Temperature range: 30–250° C.
Heating rate: 10° C./min
Number of holes in the crucible: 3

EXAMPLE 4

Preparation of Form III and Form I with Solvent/antisolvent

Ratio: 0.7 mL water: 9.7 mL acetone: 3 grams venlafaxine hydrochloride

Venlafaxine hydrochloride was dissolved in water under reflux. Acetone was added. The suspension formed is refluxed additional ten minutes and exposed at room temperature overnight. Afterward the suspension is filtered, washed with about 2 mL of the same mixture of solvents.

The solid obtained is crystallized in Form III. Further drying in a rotavapor under a reduced pressure (~10 mbar) over about 45 minutes at about 60 degrees produced Form I.

EXAMPLE 5

Preparation of Form III and Form I with Solvent/antisolvent

Ratio: 3 mL methanol:mL 9.5 ethyl acetate:2.5 grams venlafaxine hydrochloride
Ratio: 3.8 mL methanol:2 mL isopropyl ether:3 grams venlafaxine hydrochloride
Ratio: 3.5 mL methanol:2 mL MTBE:3.1 grams venlafaxine hydrochloride Venlafaxine hydrochloride was dissolved in methanol under reflux. Ethyl acetate, or isopropyl ether, or MTBE was added. The suspension formed is refluxed additional ten minutes and exposed at room temperature overnight. Afterward the suspension is filtered, washed with 2 ml of the same mixture of solvents. The solid obtained is crystallized in Form III. Further drying in a rotavapor under a reduced pressure (~10 mbar) over about 45 minutes at about 60 degrees produced Form I.

EXAMPLE 6

Preparation of Form III and Form I/II with Solvent/antisolvent

Ratio: 12 mL chloroform:5 ml hexane:2.5 grams venlafaxine hydrochloride
Ratio: 6 mL ethanol:9 ml ethyl acetate:3 grams venlafaxine hydrochloride
Ratio: 12 mL chloroform:5 ml toluene:2.6 grams venlafaxine hydrochloride Venlafaxine hydrochloride was dissolved in the solvent under reflux. The antisolvent was added. The suspension formed is refluxed additional ten minutes and exposed at room temperature overnight. Afterward the suspension is filtered, washed with 2 ml of the same mixture of solvents. The solid obtained is crystallized in Form III. Further drying in a rotavapor under a reduced pressure (~10 mbar) over about 45 minutes at about 60 degrees produced mixtures of Form II, or Form I., or a mixture of the two forms.

EXAMPLE 7

Preparation of Form III, and Form I/Form II by Direct Crystallization

Venlafaxine hydrochloride (2 grams) was dissolved in ethanol (8 mL) or in isopropyl alcohol (10 mL) under reflux and the solution was left overnight at room temperature. The crystallized material was filtered and washed with 2 ml of the same solvent. The solid obtained is crystallized in Form III. Further drying in a rotavapor under a reduced pressure (~10 mbar) over about 45 minutes at about 60 degrees produced Form II, or Form I, or a mixture of the two forms.

EXAMPLE 8

Preparation of Form IV and Form I/II by Direct Crystallization

Venlafaxine hydrochloride (2 grams) was dissolved in DMF or DMSO (8 ml) under reflux and the solution was left overnight at room temperature. The crystallized material was filtered and washed with 2 ml of the same solvent. The solid obtained is crystallized in Form III. Further drying in a rotavapor under a reduced pressure (~10 mbar) over about 45 minutes at about 60 degrees produced Form II, or Form I, or a mixture of the two forms.

EXAMPLE 9

Preparation of Form I by with Solvent/antisolvent

Ratio: 0.5 mL water:13 mL DMF:3 grams venlafaxine hydrochloride
Ratio: 0.5 mL water:13 mL DMSO:3.1 grams venlafaxine hydrochloride Venlafaxine hyrdrochloride was dissolved in water under reflux. The antisolvent was added. The suspension formed is refluxed additional ten minutes and exposed at room temperature overnight. Afterward the suspension is filtered, washed with 2 mL of the same mixture of solvents. The solid obtained is crystallized in Form I. Further drying in a rotavapor under a reduced pressure (~10 mbar) over about 45 minutes at about 60 degrees produced Form I.

EXAMPLE 10

Preparation of Form II by with Solvent/antisolvent
Ratio: 10 mL methanol:30 mL ethyl acetate:3 grams venlafaxine hydrochloride Venlafaxine hydrochloride was dissolved in methanol at about 0–5° C. The antisolvent was added. The suspension formed is stirred for 30 minutes. Afterward the suspension is filtered, washed with 2 ml of the same mixture of solvents. The solid obtained is crystallized in Form II. Further drying in a rotavapor under a reduced pressure (~10 mbar) over about 45 minutes at about 60 degrees produced Form II.

EXAMPLE 11

Preparation of Form II by Heating Form III in Static Oven

A sample of Form III was kept in a static oven at about 160 degrees for about ½ hour. The resulting polymorphic form was Form II.

EXAMPLE 12

Preparation of Form I by Heating Form IV in Static Oven

A sample of Form IV was kept in a static oven at about 160 degrees for about ½ hour. The resulting polymorphic form was Form I.

EXAMPLE 13

Preparation of Form III by Trituration of Form I

A sample of venlafaxine hydrochloride Form I (2 grams) was triturated in isopropyl ether, or hexane, or ethyl acetate (8 mL) under reflux conditions for about 1 hour or at room temperature overnight. The solid contained solvated Form III.

V) Preparation of Venlafaxine Hydrochloride from Venlafaxine Base and HCl Gas in Acetone The present invention provides a process for preparing venlafaxine hydrochloride. The process comprises exposing venlafaxine base to gaseous hydrochloric acid (HCl).

Figure 10:
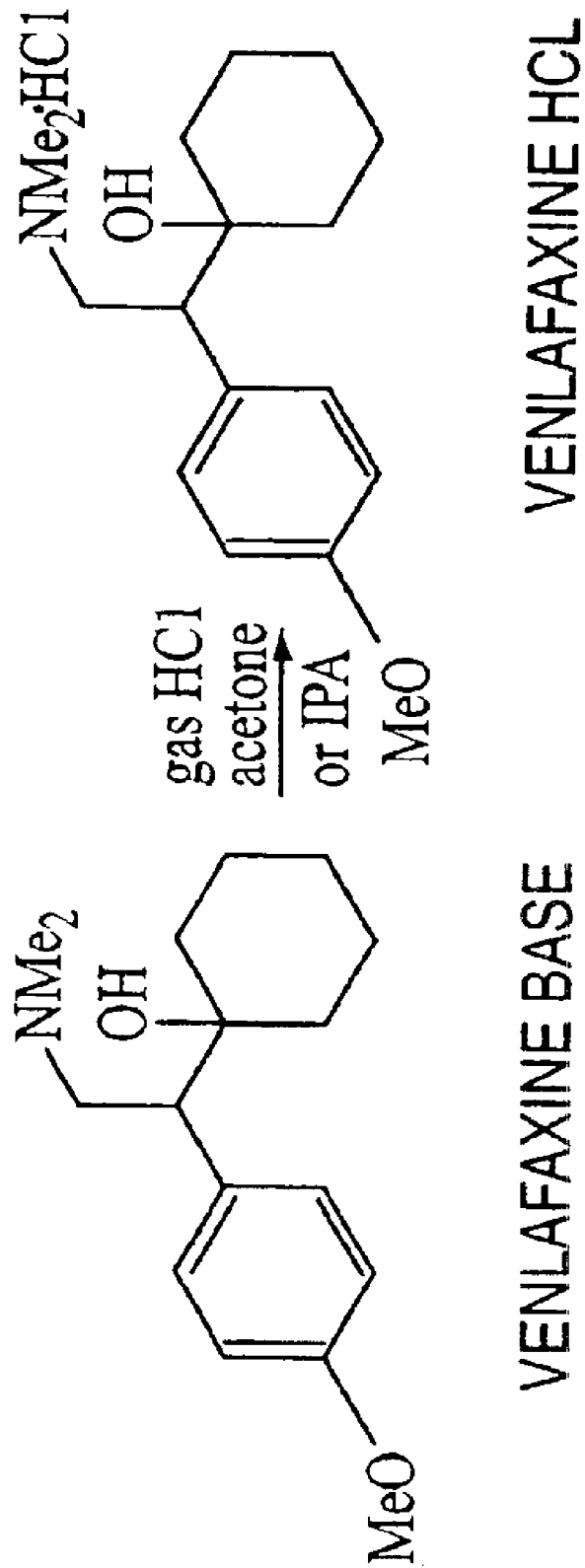
FIG. 10 represents the schematic process for preparing Venlafaxine Hydrohloride from Venlafaxine Base in the presence of Hydrochloride Acid (HCl) gas and acetone.

The schematic process for preparing venlafaxine hydrochloride from venlafaxine base is illustrated in FIG. 10.

EXAMPLE 14

Preparation of Venlafaxine Hydrochloride Crude

The reagents and solvents required for the preparation of venlafaxine hydrochloride from venlafaxine base is summarized in Table 1.

TABLE 1

| Reagents and solvents | | | |
|---|---|---|---|
| 1. Venlafaxine base | 27.7 grams | 100 mmol | 1.0 eq |
| 2. HCl, gas | | | |
| 3. Acetone | 846 grams | | |

The theoretical yield of the product, (i.e., venlafaxine hydrochloride) is about 31.34 grams (i.e., 100 mmol).

A 1-L double-jacketed reactor equipped with a mechanical stirrer, a thermometer, a pH-electrode and PTFE deep tube was charged with venlafaxine base (about 27.7 grams) and acetone (about 526 grams). The mixture was stirred for about 20 min at room temperature until a homogeneous solution was achieved.

The solution was acidified with gaseous hydrogen chloride at about 10° C. under vigorous stirring to achieve about pH 2.0. The resulting suspension was stirred for about 2 hours at about 10° C.

The precipitated crystals were filtered off, washed on filter with cold acetone (about 120 grams) and dried under reduced pressure at about 50° C. (water bath) to a constant weight to give about 29.57 grams (about 94.4%) of white crystals of venlafaxine hydrochloride with about 99.92% purity by HPLC.

EXAMPLE 15

Preparation of Venlafaxine Hydrochloride (Form I)

The crude venlafaxine hydrochloride (about 15.0 grams) was triturated with acetone (about 60.0 grams) for about 1 hour at about 60° C. and for about 1 hour at about 0° C., filtered off, washed on filter with cold acetone (about 120 grams) and dried upon stirring under reduced pressure at about 50° C. (water bath) to a constant weight to give about 14.8 grams (about 93.2%) of venlafaxine hydrochloride as white crystals with purity of about 99.95% by HPLC.

EXAMPLE 16

Preparation of Venlafaxine Hydrochloride (Form II)

The crude venlafaxine hydrochloride (about 15.0 grams) was triturated with acetone (about 60.0 grams) for about 1 hour at about 60° C. and for about 1 hour at about 0° C., filtered off, washed on filter with cold acetone (about 120 grams) and dried in a tray under reduced pressure at about 50° C. (water bath) to a constant weight to give about 14.8 grams (about 93.2%) of venlafaxine hydrochloride as white crystals with purity of about 99.95% by HPLC.

EXAMPLE 17

Preparation of Venlafaxine Hydrochloride Form (I)

Venlafaxine base (1 Kg) was dissolved in isopropanol (6 L). Hydrochloric acid (gas) was bubbled until a pH ranging from about pH 5 to about pH 8 was achieved, at ~20° C. Preferably, the pH ranges from pH about 6 to pH about 7.5. Most preferably, the pH is at about pH 7. The reaction mixture was heated to clear solution and cooled gradually to 10° C. The precipitate was filtered and washed with isopropanol and dried in vacuum.

The present invention is not to be limited in scope by the specific embodiments described herein. Indeed, various modifications of the invention can be appreciated in addition to those skilled in the art from the foregoing description and accompanying figures. Such modifications are intended to fall within the scope of the claims.

What is claimed is:

1. A process for preparing venlafaxine hydrochloride Form I, comprising the steps of:
   1) providing a mixture of venlafaxine in isopropanol; and
   2) introducing hydrochloric acid until a pH is in the range of pH about 5 to about 8.

2. The process according to claim 1, wherein the pH is between pH about 6 to about 7.5.

3. The process according to claim 1, wherein the pH is about 7.

4. The process according to claim 1, wherein the hydrochloric acid is a gaseous hydrochloric acid.

5. The process according to claim 1, wherein the venlafaxine is a venlafaxine base.

6. The process according to claim 1, wherein the mixture is a homogeneous solution of venlafaxine.

* * * * *